United States Patent [19]
Bhagavan et al.

[11] Patent Number: 5,589,338
[45] Date of Patent: Dec. 31, 1996

[54] NUCLEIC ACIDS ENCODING A MUTANT FORM OF HUMAN SERUM ALBUMIN INVOLVED IN FAMILIAL DYSALBUMINEMIC HYPERTHYROXINEMIA

[75] Inventors: Nadhipuram V. Bhagavan; Charles E. Petersen; Morton Mandel, all of Honolulu, Hi.

[73] Assignee: University of Hawaii, Honolulu, Hi.

[21] Appl. No.: 380,366

[22] Filed: Jan. 30, 1995

Related U.S. Application Data

[62] Division of Ser. No. 215,135, Mar. 21, 1994.

[51] Int. Cl.$^6$ .............................. C12Q 1/68; C12P 19/34; C07H 21/04
[52] U.S. Cl. ..................... 435/6; 435/91.2; 435/69.6; 435/70.1; 435/240.2; 435/320.1; 536/23.5
[58] Field of Search ........................... 435/6, 91.2, 69.1, 435/69.6, 70.1, 71.1, 240.2, 320.1, 252.3; 536/23.5, 24.33

[56] References Cited

U.S. PATENT DOCUMENTS

| | | | |
|---|---|---|---|
| 4,683,202 | 7/1987 | Mullis | 435/91 |
| 4,914,027 | 4/1990 | Knapp et al. | |
| 5,100,784 | 3/1992 | Latta et al. | 435/69.7 |
| 5,187,261 | 2/1993 | Latta et al. | 530/363 |
| 5,380,712 | 1/1995 | Ballance et al. | |

OTHER PUBLICATIONS

Petersen et al., *J. Med. Genet.* 31(5), 355–359 (May 1994).
Sunthornthepvarakul et al., *Bioch. Biophys. Res. Comm.* 202(2), 781–787 (1994 Jul.).
Minghetti et al., *J. Biol. Chem.* 261(15), 6747–6757 (1986).
Takamatsu et al., *Bull. Osaka Med. Coll.* 36(1,2), 35–45 (1990).
Yabu et al., *J. Clin. Endo. Metab.* 60(3), 451–459 (1985).
Lalloz et al., *Clin. Endo.* 18, 11–24 (1983).
Lawn, Richard M. et al., "The sequence of human serum albumin cDNA and its expression in *E. coli*," Nucleic Acids Research (1981) 9(22):6103–6115.
Magnus, T. M. et al., "Thyroid Hormone Resistance in Hibernating Ground Squirrels, *Spermophilus richardsoni*," *General and Comparative Endocrinology* (1988) 69:352–360.
Takamatsu, J. et al., "Diagnosis of Familial Dysalbuminemic Hyperthyroxinemia and Investigation of the Nature of the Variant Albumin," *Bulletin of the Osaka Medical College* (1990) 36(1,2):35–45.
Dughie, "Fluorescence Investigations of Albumin From Patients With Familial Dysalbuminemic Hyperthyroxinemia", *Photochem. Photobiol.*, 57:416–19 (1993).

*Primary Examiner*—Kenneth R. Horlick
*Attorney, Agent, or Firm*—Morrison & Foerster LLP

[57] ABSTRACT

Modified forms of human serum albumin (HSA) wherein the arginine at position 218 is substituted by a less basic amino acid show strong thyroxin-binding activity. Recombinant materials for production of these modified forms of HSA and fragments are disclosed, as well as recombinant materials for diagnosis for the presence or absence of a gene encoding said modified HSA.

7 Claims, No Drawings

NUCLEIC ACIDS ENCODING A MUTANT FORM OF HUMAN SERUM ALBUMIN INVOLVED IN FAMILIAL DYSALBUMINEMIC HYPERTHYROXINEMIA

This application is a division of application Ser. No. 08/215,135 filed Mar. 21, 1994.

TECHNICAL FIELD

The invention is directed to proteins that specifically bind target molecules. More specifically, the invention concerns peptides and proteins that bind to thyroxin.

BACKGROUND ART

Hyperthyroidism and its accompanying symptoms appears to affect approximately 1% of the population in the developed world. One cause of hyperthyroidism is Grave's Disease in which antibodies that stimulate the thyroid gland are overproduced. The negative effects of this condition include irritability, insomnia, and enhanced risk of congestive heart failure and atherosclerosis.

Current treatments include small-molecule drugs such as propylthiouracil and methimazole which counteract the action of thyroxin, surgery to remove all or part of the thyroid gland, and administration of radioiodide to diminish its function.

None of these approaches is completely satisfactory. The mechanism of counteraction of thyroxin by various antithyroxin drugs is unclear; surgery and radioisotope treatments are inherently risky. Thus, it would be helpful to provide a drug that lowers the thyroxin concentration in the serum without deleterious side effects.

The proteins and peptides of the present invention provide such a solution. They are closely related to a native protein, human serum albumin, and thus would be expected to have negligible side effects. Forms of HSA having only a minor modification at position 218 and fragments which contain this modification are capable of binding free thyroxin thus causing its inactivation.

One of these modified forms occurs naturally in familial dysalbuminemic hyperthyroxinemia (FDH). This is an autosomal dominant syndrome in subjects who have an elevated total serum thyroxin concentration but are clinically euthyroid. It is known that the elevated total thyroxin levels in serum in these patients is due to the presence of deviant HSA that exhibits enhanced binding to thyroxin.

Previous work by the present applicants based on intrinsic fluorescence properties of purified normal HSA and HSA obtained from an FDH patient using both steady-state and time-resolved methodologies showed that the patient had two HSA species with different affinities for thyroxin (Dughie, C. et al. *Photochem Photobiol* (1992) 57:416–419). The modification responsible for the thyroxin affinity of modified HSA has now been found. Thus, the invention provides, in purified and isolated form, modified forms of HSA and fragments thereof that are useful in diagnostic and therapeutic contexts.

DISCLOSURE OF THE INVENTION

The invention is directed to proteins and peptides which are capable of binding thyroxin with high affinity. Accordingly, these proteins and peptides are useful to lower the thyroxin levels in serum as well as reagents for the determination of thyroxin concentrations in biological or other samples. In addition, the invention provides DNA corresponding to the DNA that natively encodes one of the proteins of the invention. The invention also is directed to a method to diagnose FDH patients by subjecting human leukocyte DNA to the polymerase chain reaction (PCR) to detect the presence of the altered gene.

Thus, in one aspect, the invention is directed to a compound in purified and isolated form which is a modified form of human serum albumin (HSA) wherein said modification comprises the substitution for arginine at position 218 of said HSA an amino acid of lower basicity, and fragments of said modified HSA which contain said modification and which exhibit thyroxin-binding activity at least 10% of that of the corresponding full-length modified HSA.

In other aspects, the invention is directed to recombinant materials useful for the production of the compounds of the invention and to methods for its recombinant production. In still other aspects the invention concerns methods to determine thyroxin concentration in assays involving detection of the complex formed by the compound of the invention with thyroxin present in the sample.

In still other aspects, the invention is directed to DNA or other nucleic acids comprising a nucleotide sequence corresponding to the nucleotide sequence that natively encodes modified HSA or a fragment thereof. These corresponding DNAs may be useful in modulating the production of the modified HSA, as primers in systems for amplification or as probes.

Finally, in another aspect, the invention is directed to a method to diagnose FDH patients using amplification techniques such as PCR.

MODE OF CARRYING OUT THE INVENTION

The complete amino acid sequence and the nucleotide sequence natively encoding human serum albumin are known. Latta, et al. U.S. Pat. Nos. 5,100,784 and 5,187,261, the disclosures of which are incorporated herein by reference, disclose these complete sequences. As shown in FIG. 5 of the '261 patent, for example, an arginine residue occupies the position shown there as position 218 of this protein.

The invention includes modified forms of this protein where this arginine is replaced by a less basic amino acid. The invention also includes fragments of this modified form which include the modified sequence and which have the capacity to bind thyroxin at least 10% of that shown by the corresponding full-length modified HSA.

X-ray crystallographic data for native HSA published by He, X. M. et al. *Nature* (1992) 358:209–215, have established that the structure is divided into three homologous domains: 1, 2 and 3, each divided into two subdomains, a and b, where there are two principal hydrophobic binding pockets in subdomains 2a and 3a. Binding to hydrophobic ligands appears to occur in these subdomains. Position 218, the critical position, is located in subdomain 2a.

Preferred substitutions for arginine at this position are those which are unlikely to distort the conformation of the protein and which preserve the thyroxin-binding character of the HSA isolated from FDH patients.

Accordingly, preferred amino acid substitutions include the relatively small amino acids Gly, Ser, Cys and Ala, and the relatively polar amino acids Gln, Asn and Thr. Less preferred are the hydrophobic amino acids Ile, Val, Glu and Met. Still less preferred are the acidic amino acids Asp and Glu and the aromatic amino acids Trp, Phe and Tyr. As Pro may have a significant effect on conformation, Pro is less preferred also. As described hereinbelow, the form found in FDH patients contains a His residue rather than Arg.

PREPARATION OF THE INVENTION COMPOUNDS

The full-length modified HSA of the invention contains 585 amino acids. While it is possible theoretically to synthesize this protein using standard solid-phase synthesis techniques, such syntheses are laborious and would involve synthesis of segments of the molecule followed by ligation of the individual peptides. In a much preferred method of providing the full-length modified HSA of the invention, recombinant methods are employed. These are by now well established in the art. Synthetic DNA techniques are sufficiently advanced that preparation of a DNA encoding the 585 amino-acid protein can be accomplished using commercial equipment. If the DNA is prepared synthetically, any of the degenerate sequences which encode the known amino acid sequence of the modified HSA may be employed, and choice of codons is governed by the desired host. Alternatively, the DNA encoding HSA can be isolated either as cDNA as genomic DNA as described hereinbelow and modified by site-directed mutagenesis to provide DNA encoding the modified form.

The appropriate DNA encoding the modified full-length HSA is then inserted into a suitable expression system for production of HSA in the desired host. While procaryotic hosts such as *E. coli* could be employed using conventional control sequences including, if desired,. inducible promoters, production in eucaryotic hosts is preferred since appropriate folding is more readily achieved. Production of recombinant proteins in eucaryotic hosts is well established and has been conducted on a commercial scale for more than ten years. Suitable eucaryotic hosts include yeasts; insect cells, in particular employing the bacculoviral expression system; mammalian cells such as Chinese hamster ovary cells or other appropriate cell lines employing, generally, either viral or mammalian promoters, and, if desired, additional expression regulators such as enhancers. The construction of such expression systems is by this time standard and the choice of expression system and host appropriate to the production of the full-length modified HSA a matter of standard optimization.

The modified HSA can be recombinantly produced with the mature protein optionally ligated at the N-terminus to an appropriate signal sequence to effect secretion of the mature protein. Either the signal sequence normally associated with HSA may be employed, or a heterologous signal sequence compatible with the host may be used. A number of such signal peptides are known in the art, including the α factor signal peptide for yeast. Alternatively, the protein can be obtained intracellularly and recovered through lysis of the cells.

In any event, the appropriate DNA encoding the modified HSA is ligated into a suitable expression system and host cells compatible with the expression system are modified to contain it. The cells are cultured under conditions which effect the expression of the HSA-encoding nucleotide sequence and the HSA is recovered from the medium and purified and isolated according to standard technology. If secreted into the medium, the purification is simplified due to the relative lack of contamination proteins. Standard purification techniques such as ammonium sulfate precipitation, ion exchange chromatography, affinity chromatography, reverse-phase chromatography, gel filtration, and the like are employed.

Fragments

For production of thyroxin-binding fragments, similar preparation techniques may be used but these are simplified by the smaller size of the peptide or protein. The fragments will contain the position modified in the modified HSA and will retain ability to bind thyroxin which is at least 10% of the thyroxin-binding activity of the corresponding full-length modified HSA. By "corresponding" full-length modified HSA is meant that HSA which contains the same modification at position 218 as does the fragment. Preferred fragments include peptides having amino acid sequences found between positions 190–585; 190–487; 190–390; and 190–292 inclusive. Also preferred is the fragment which represents positions 97–292. Shorter versions of these specified fragments containing 1–10 fewer amino acids than those specified may also be employed.

The fragments are verified to have the requisite thyroxin-binding ability using standard thyroxin-binding assays. Preliminary screening can be done using qualitative assays. To assess conformance with the thyroxin-binding requirement according to the invention, quantitation may be required. For example, a dissociation constant for the protein or peptide with respect to thyroxin can be determined using known concentrations of the protein or peptide and of labeled thyroxin and determining the ratio of labeled to unlabeled thyroxin in the sample. The dissociation constant is then determined for the full-length modified protein of the invention, and for the fragment. Within the scope of the invention are fragments having dissociation constants no greater than 10 times the dissociation constant for the corresponding modified full-length HSA. These are defined herein as having capacity to bind thyroxin at least 10% of that shown by the corresponding full-length modified HSA.

RECOMBINANT MATERIALS

As described above, DNA encoding the peptides and proteins of the invention can readily be synthesized or recovered for use in recombinant production of the modified HSA or fragment. In addition, nucleic acids "corresponding to" DNA natively involved in expressing the modified HSA or fragment are useful in other contexts as well. By "corresponding to" is meant either that the same nucleotide sequence as the native DNA is present in the nucleic acid molecule or its complement is present, or a sequence designed on the basis of the native sequence is present. For example, formation of triple helixes using single-stranded oligomers that bind to duplex DNA obeys binding rules different from those of complementarity but nevertheless specific for the targeted duplex. Thus, the relevant "corresponding" nucleic acid would contain a nucleotide sequence which is capable of forming a triple helix with the natively occurring duplex. By "native" nucleotide sequence is meant that sequence which is involved in the production of HSA in humans or the relevant region thereof modified only at position 218 to provide the less basic amino acid codon. Sequences involved in production of modified HSA include the coding regions of the gene, exon regions which are transcribed but not translated, introns in the HSA genome, and regulatory regions such as promotion regions that are unique to the HSA gene.

Using the native sequence as a guide, then, for example, primers may be designed for amplification of the relevant region of the gene to permit genetic testing for the presence or absence of FDH in human subjects. As described hereinbelow, position 218 occurs in exon 7 of the genomic DNA. As described below, suitable primers can be constructed based on the nucleotide sequence of the surrounding introns to amplify this exon in its entirety or only a portion of the exon may be amplified. If the amplified fragment is small enough, the presence or absence of the modified amplified portion can be detected using a suitable oligonucleotide which exactly matches the modified form. Preferably, however, the presence or absence of the modified form can be ascertained as illustrated below by the presence of an HphI site in the amplified exon. Persons containing the modification exhibit this site in the relevant region. This provides a simple method for diagnosing the presence or absence of the modified gene.

It is also possible that the production of the modified HSA in subjects with FDH may also be modulated by antisense or triple helical binding techniques the relevant corresponding nucleic acids.

Methods of Using the Peptides and Proteins of the Invention

The compounds of the invention can be used to detect the presence or absence, or the concentration, of thyroxin in a sample in a manner analogous to antibodies or antibody fragments specific for thyroxin. In principle, the thyroxin-binding compounds of the invention are used as specific binding partners for thyroxin in standard immunoassay-type procedures for determination of thyroxin. A wide variety of experimental designs and protocols is conventional for such assays, including direct and competitive formats, sandwich assays, and the like. Detection methods for measuring the formation of the complex between the thyroxin-binding compounds of the invention and thyroxin include radioisotope labeling, enzyme labeling, fluorescence labeling and combinations of these.

Thus, for example, in one illustrative assay format, the compound of the invention is coupled to solid support either by adsorption or using standard covalent binding techniques and the sample in which thyroxin is to be measured is mixed with labeled thyroxin. The mixture is incubated with the derivatized solid support and the solid support is then removed and washed. The level of thyroxin in the sample is determined either by measuring the amount of label bound to solid support (an inverse correlation with thyroxin concentration) or the amount of thyroxin remaining unbound is measured (direct correlation). The foregoing is, of course, merely illustrative and a wide variety of other protocols, including protocols designed for homogeneous media, may be employed.

In addition to use in thyroxin-binding assays, the compounds of the invention may be used to lower the thyroxin levels of an animal subject. Animal subjects include humans and domestic animals or livestock with elevated thyroxin levels. For use in this method, the compounds of the invention are typically formulated into pharmaceutical or veterinary compositions designed for the appropriate route of administration. Accordingly, the compounds of the invention are mixed with suitable pharmaceutically acceptable excipients or diluents such as those described in *Remington's Pharmaceutical Sciences*, latest edition, Mack Publishing Company, Easton, Pa.

In general, systemic administration is preferred. Injection is the most direct approach and may be intravenous, intramuscular, subcutaneous, intraperitoneal and the like. In addition, slow release formulations which can be supplied as implants or suppositories may also be employed. Suitable routes of administration will be evident to those of ordinary skill and optimization can be accomplished using routine experimentation.

Suitable subjects for treatment using the compounds of the invention include any subject where it is desirable to lower the level of thyroxin circulating. These include human patients with Graves' Disease, but may also include others with temporary conditions of hyperthyroidism, as well as nonhuman animals with this condition.

The compounds of the invention, can, of course, be used in combination with other medication and may be formulated into compositions which contain more than one active ingredient or more than one modified form of HSA or its fragments.

The following examples are intended to illustrate but not to limit the invention.

EXAMPLE 1

Comparison of the Genomic Sequences of Normal and FDH HSA

Individual exons of the HSA gene obtained from DNA extracted from leukocytes of FDH patients and a normal patient were amplified and compared as follows:

Whole blood drawn in EDTA was obtained from a normal and FDH patient as described by Scottolini, A. G. et al. *Clin Chem* (1984) 30:1179–1181. Five ml leukocyte separation buffer (Sigma Histopake Type 1119) was layered under 15 ml of the whole blood and the layer centrifuged at 400×g for 30 minutes The mononuclear cell layer was collected and genomic DNA purified using a DNA extraction kit (Oncor Nonorganic DNA Extraction Kit). Sets of 24-mer primer pairs were designed complementary to known intron DNA sequences on either side of each of the 14 coding exons of HSA (Minghetti, P. P. et al. *J Biol Chem* (1986) 261:6747–6757). A fragment was generated using PCR for each exon from a 50 µl reaction mixture containing 1×PCR buffer (Perkin-Elmer) and 200 µM dATP, TTP, dCTP and dGTP (Epicenter), 1 µM each primer (Midland) 500 ng genomic DNA, and 2.5 U *Thermos aquaticus* DNA polymerase (Perkin-Elmer). Each reaction was overlaid with one drop mineral oil, and amplification carried out for 40 cycles of 30 seconds at 94° C., 30 seconds at 55° C., 2 minutes at 72° C. Each fragment was separated using the Qiagen, PCR Purification Spin Kit.

The amplified fragments were sequenced directly using the same primers as the Promega, fM Sequencing System with direct incorporation of [alpha-hu 35S]dATP (New England Nuclear) according to the kit instructions with the following changes in the sequencing cocktail; 5 pM of the appropriate primer was used instead of 3 pM and 20 µCuries of [alpha-$^{35}$S]dATP was used instead of 5µ Curies. The same temperature cycling profile was used as in template synthesis except only 30 cycles were run for sequencing. The reaction products were heat denatured in formamide loading buffer and electrophoresed in 6% acrylamide gels containing 7M urea and 1X TBE (0.090M Tris-borate, 0.002M EDTA, pH 8.0) and autoradiographed.

All 14 exons were amplified and sequenced from genomic DNA purified from an FDH patient and the normal volunteer. Lanes corresponding to each exon were scanned for any variation between the normal and FDH-derived exons. A mutation was found in exon 7 of the FDH patient.

Exon 7 from a normal HSA gene does not contain an HphI site whereas a mutation identified in two FDH patients creates an HphI site. This was verified by precipitating the amplified exon 7 fragments in 75% absolute ethanol and resuspending them i 20 µl of HphI digestion buffer, adding 10 U of HphI (New England Biolabs) and incubating for 6 hours at 37° C. Samples were electrophoresed in a 3% agarose (FMC BioProducts, Metaphor Agarose) gel in 1X TAE (0.04M Tris-acetate, 0.001M EDTA, pH 8.0) and bands were visualized by staining with ethidium bromide.

The sequence for HSA from the normal subject matched the published HSA sequence completely. HSA from an FDH patient contained a G to A transition resulting in converting position 218 of mature HSA from Arg(CGC) to His(CAC). Both the modified and unmodified DNAs were found in two FDH patients tested, indicating heterozygosity; thus HphI digestion of exon 7 fragments derived from both FDH patients was incomplete.

EXAMPLE 2

Confirmation from Isolated Protein Studies

HSA was purified from the plasma of an FDH patient and a normal volunteer by subjecting the plasma to ammonium sulfate precipitation at 50% saturation, precipitating the HSA by lowering the pH to the isoelectric point of pH 4.4 at 2°–4° C. The HSA precipitate was delipidated by reaction with Norita activated charcoal at pH 3 and then dialyzed against water and then against 0.04M sodium phosphate buffer pH 7.5.

The HSA was loaded in PBS onto a sepharose CL-6B (Sigma) cibachron blue affinity column equilibrated in PBS. (PBS is 0.15M NaCl, 0.04M sodium phosphate, pH 7.5.) The column was washed with 20 bed volumes of PBS and the bound HSA eluted with 3M NaCl. The eluent was dialyzed against water and lyophilized in the purity of HSA determined by SDA Page.

Purified HSA from the FDH patient and commercial HSA were alkylated using standard procedures and desalted by preparative HPLC. The purified samples were digested with trypsin and the digests were injected into analytical HPLC columns (Vydek, C-18 protein/peptide) equilibrated in 0.1% TFA, 9% acetonitrile. After injection, the column was washed for 15 minutes with equilibration buffer and the acetonitrile concentration increased by linear gradient at a rate of 0.33% per minute. The absorbance of the eluent was monitored at 230 nm.

The chromatogram of the FDH HSA trypsin digest showed an initial peak not present in the commercial HSA digest. This peak was sequenced using standard Edman degradation methods and had the sequence AWAVAHLSQR, confirming an Arg-to-His substitution at position 218.

EXAMPLE 3

Assay for Thyroxin-Binding Activity

The assay uses a radioimmunoassay kit provided by Clinical Assays, Stillwater, Minn., designed to measure free $T_4$ levels in clinical samples. In the assay, $T_4$ antibody is immobilized on the lower inner surface of a tube and a sample to be assayed is added along with a fixed amount of $T_4$ tracer labeled with $^{125}I$. The competitive assay results in an inverse correlation between free $T_4$ concentration and radioactivity associated with antibody.

This assay was adapted to measure HSA affinity for $T_4$ tracer. To each assay tube, 1 ml tracer buffer and the $T_4$ tracer were added followed by 250 µg of HSA in 15 µl water. The tubes were incubated 90 minutes at 37° C. and the fluid aspirated off. The amount of radioactivity remaining is measured in an Isodata Gamma counter.

Addition of either HSA purified from a normal volunteer or commercial HSA to the assay did not reduce the amount of $T_4$ associated with $T_4$ antibodies; however, HSA purified from an FDH patient significantly reduced this amount. These results are shown for duplicate samples and recorded as the CPM measured, as shown in Table 1.

TABLE 1

| Sample | CPM |
| --- | --- |
| No HSA | 24,355 |
|  | 23,659 |
| Commercial HSA | 24,423 |
|  | 22,456 |
| Normal HSA | 26,649 |
|  | 22,798 |
| FDH HSA | 12,426 |
|  | 11,542 |

As shown in Table 1, FDH HSA substantially reduces the radioactivity found to the antibody, thus indicating that FDH HSA competes successfully with antibody for the $T_4$ tracer.

We claim:

1. An isolated DNA molecule that comprises a nucleotide sequence that encodes modified HSA wherein said modification is the substitution for arginine at position 218 of said HSA, of an amino acid of lower basicity, or encodes a fragment of said modified HSA which contains said modification and which exhibits thyroxin-binding activity at least 10% of that of the corresponding full-length modified HSA.

2. An isolated DNA molecule effective when contained in a compatible host cell to express a nucleotide sequence encoding a modified HSA wherein said modification is the substitution for arginine at position 218 of said HSA, of an amino acid of lower basicity, or encoding a fragment of said modified HSA which contains said modification and which exhibits thyroxin-binding activity at least 10% of that of the corresponding full-length modified HSA, which DNA molecule comprises a nucleotide sequence encoding said modified HSA or fragment operably linked to control sequences which effect expression.

3. A host cell transfected, infected or transformed with the DNA molecule of claim 2.

4. A method to produce a modified HSA or fragment thereof which method comprises culturing the cells of claim 3 under conditions favorable to expression of said encoding nucleotide sequence so as to effect production of said modified HSA or fragment thereof; and recovering said modified HSA or fragment from the culture.

5. An isolated DNA molecule comprising a nucleotide sequence that corresponds to a nucleotide sequence natively involved in producing modified HSA or a fragment thereof wherein said modification is substituting a histidine for the arginine at position 218.

6. A method to detect the presence of familial dysalbuminemic hyperthyroxinemia (FDH) in a subject which method comprises amplifying a region of DNA which has been obtained from said subject to form amplification products, wherein said region comprises at least a portion of exon 7 of the HSA gene; and detecting the presence or absence in said amplification products of a DNA sequence encoding modified HSA, wherein said modification is the substitution of histidine for arginine at position 218, wherein the presence of said sequence is indicative of FDH.

7. The method of claim 6 wherein said detecting is conducted by determining the susceptibility of the amplification products to digestion by HphI.

* * * * *